US005589604A

United States Patent [19]
Drohan et al.

[11] Patent Number: 5,589,604
[45] Date of Patent: Dec. 31, 1996

[54] EXPRESSION OF HUMAN PROTEIN C IN MAMMARY TISSUE OF TRANSGENIC MAMMALS

[75] Inventors: William N. Drohan, Springfield; Tracy D. Wilkins, Blacksburg; William H. Velander, Blacksburg; John L. Johnson, Blacksburg, all of Va.

[73] Assignees: American Red Cross, Washington, D.C.; Virginia Intellectual Property Division, Blacksburg, Va.

[21] Appl. No.: 247,484

[22] Filed: May 23, 1994

Related U.S. Application Data

[63] Continuation of Ser. No. 638,995, Jan. 11, 1991, abandoned.
[51] Int. Cl.$^6$ ............... C12N 5/00; C12N 15/00; C12N 9/48; C12P 21/04
[52] U.S. Cl. ............... 800/2; 435/69.6; 435/212
[58] Field of Search ............... 800/2; 435/172.3

[56] References Cited

U.S. PATENT DOCUMENTS 4,775,624  10/1988  Bang et al. .
4,873,316  10/1989  Meade et al. .
4,992,373  2/1991  Bang et al. .

FOREIGN PATENT DOCUMENTS 0264166  4/1988  European Pat. Off. .
0279582  8/1988  European Pat. Off. .
WO88/00239  1/1988  WIPO .
WO88/01648  3/1988  WIPO .
WO90/05188  5/1990  WIPO .

OTHER PUBLICATIONS

Colpan et al (1984) "High Performance Liquid Chromatography of High–Molecular Weight Nucleic Acids . . . " 296, 339–353.
Clark et al (1987) Tibtech 5, 20–24.
Velander et al (1992) Proced. Natl. Acad. Sci, 89, 12003–12007.
Henninghausen (1990) Protein Exp. and Purif. 1, 3–8.
Grinnell et al (1990) Regulation and Prod. of Anticoag., 29–63.
Yan et al (1989) TIBS 14, 264–268.
Grinnell et al (1987) Bio/Technology 5, 1189–1192.
Pittrus et al (1988) Proced. Natl. Acad. Sci. 85, 5874–5878.
Hogan et. al. (1986) *Manipulating the Mouse Embryo*, Cold Spring Harbor Laboratory, Cold Spring Harbor, NY 153–203.
Denman et al. (Sep. 1991) *Bio/Technology* 9: 839–843, "Transgenic Expression of a Variant of Human tPA in Goat Milk: Purification and Characterization of the Recombinant Enzyme".
Ebert et al. (Sep. 1991) *Bio/Technology* 9: 835–838, "Transgenic Production of a Variant of Human tPA in Goat Milk: Generation of Transgenic Goats and Analysis of Expression".
Gordon et al. (Nov. 1987) *Bio/Technology* 5: 1183–1187, "Production of Human Tissue Plasminogen Activator in Transgenic Mouse Milk".
Krimpenfort et. al. (Sep. 1991) *Bio/Technology* 9: 844–847, "Generation of Transgenic Dairy Cattle Uisng 'In Vitro' Embryo Production".
Walls et al. (1989) *Gene* 81: 139–149, "Amplification of Multicistronic Plasmids in the Human 293 Cell Line and Secretion of Correctly Processed Recombinant Human Protein C".
Wright et al. (Sep. 1991) *Bio/Technology* 9: 830, "High Level Expression of Active Human Alpha–1–Antitrypsin in the Milk of Transgenic Sheep".
Yan et al. (Jul. 1990) *Bio/Technology*: 8 655–661, "Characterization and Novel Purification of Recombinant Human Protein C from Three Mammalian Cell Lines".

*Primary Examiner*—Deborah Crouch
*Attorney, Agent, or Firm*—Foley & Lardner

[57] ABSTRACT

Recombinant protein C characterized by a high percentage of active protein can be obtained in the milk of transgenic mammals that incorporate DNAs according to the present invention. Transgenic mammals of the present invention are produced by introducing into developing embryos DNA that encodes protein C, such that the DNA is stably incorporated in the DNA of germ line cells of the mature mammals and inherited in normal, mendelian fashion.

20 Claims, 5 Drawing Sheets

EXPRESSION OF HUMAN PROTEIN C IN MAMMARY TISSUE OF TRANSGENIC MAMMALS

This application is a continuation of application Ser. No. 07/638,995, filed Jan. 11, 1991, now abandoned.

The present invention relates to the production of natural and modified forms of the human coagulation factor protein C. In particular, the invention relates to a transgenic animal containing, stably incorporated in its genomic DNA, an exogenous gene which is expressed specifically in mammary tissue, such that protein C is secreted into milk produced by the animal.

BACKGROUND OF THE INVENTION

Protein C is an important component of the coagulation system that has strong anticoagulant activity. In its active form it is a serine protease that proteolytically inactivates Factors $V_a$ and $VIII_a$.

Human protein C (hPC) is a 62 kD, disulfide-linked heterodimer consisting of a 25 kD light chain and a 41 kD heavy chain which circulates as an inactive zymogen in plasma. At the endothelial cell surface it is activated to activated protein C (APC) by limited thrombin proteolysis in the presence of thrombomodulin; cleavage of an Arg-Leu bond in the amino terminal portion of the heavy cain releases a 12 amino acid peptide. See generally Gardiner & Griffin in PROGRESS IN HEMATOLOGY, Vol. XIII at page 265–278 (Brown, Grune and Stratton, Inc. 1983).

Several regions of the molecule have important implications for function as an anticoagulant in the regulation of hemostasis. The amino terminal portion of the light chain contains the nine γ-carboxyglutamic acid (Gla) residues required for calcium-dependent membrane binding and functional activation. Another post-translational modification is β-hydroxylation of aspartic acid reside 71, possibly required for calcium-dependent membrane binding which is independent of the binding activity of the Gla regions.

There are a variety of clinical situations for which protein C may prove beneficial. It may serve as replacement therapy in homozygous deficient infants suffering from purpura fulminans neonatalis. Other conditions include patients with a previous history of warfarin-induced skin necrosis who must have additional warfarin therapy, heparin-induced thrombocytopenia, septic shock for prevention of intravascular coagulation and organ damage, and for fibrinolytic therapy, as protein C can protect tPA from plasma inhibitor proteins. Table 1 represents one estimate of the number of individual cases of several clinical syndromes which might be treated by purified protein C. Because there has not been sufficient material available from plasma for clinical trials until recently, these data are necessarily based on an incomplete assessment of the therapeutic potential for protein C.

TABLE 1

PARTIAL ESTIMATE OF U.S. CLINICAL REQUIREMENTS FOR PROTEIN C AND ACTIVATED PROTEIN C

| Indication | Estimated Dose (mg) Per Treatment | # Treatments Per Year | Total U.S. Req. (Kg) |
|---|---|---|---|
| Septic Shock | 5–50 | 120,000 | 0.6–6.0 |
| Thrombolytic Therapy** | 10–100 | 800,000 | 8–80 |
| Hip Replacement | 10–100 | 200,000 | 2–20 |
| Homozygous Deficient | 3 | 100 × 365* | 0.10 |
| Heterozygous Deficient | 50 | 1,000 | 0.05 |
| Total | | | 10.8–106.2 |

*100 individuals in U.S. × 365 treatment/year
**Refers to the use of APC, following thrombolytic therapy, to prevent the reformation of blood clots.

The gene for human protein C has been cloned and sequenced, as has bovine protein C gene. See Forster et al., Proc. Nat'l Acad. Sci. USA 82:4673 (1985); U.S. Pat. No. 4,775,624. It is synthesized as an inactive precursor that undergoes several proteolytic events during the processes of secretion and activation. First, a signal sequence as proteolytically removed upon secretion. A second proteolytic event removes the dipeptide lys156 arg157, producing the inactive zymogen, a two chain disulfide bridged protein, consisting of a light chain of 155 amino acids and a heavy chain of 262 amino acids. The zymogen is activated by a final proteolytic event that removes residues 158–169, yielding active protein C, a serine protease with potent anticoagulant activity. Beckmann et al., Nucleic Acids Res. 13:5233 (1985).

In addition to proteolytic processing, human protein C undergoes several post-translation modifications. Perhaps most salient among these modifications is the γ-carboxylation of the first nine glutamic acid residues in protein C, by a vitamin K dependent enzyme. DiScipio & Davie, Biochemistry 18:899 (1979). Gamma-carboxylation is required for anticoagulant activity, and is associated with $Ca^{2+}$-dependent membrane binding. The anticoagulant activity of protein C varies directly with the extent of γ-carboxylation, and the highest levels of activity are achieved only when γ-carboxylation of the sixth and seventh glutamic acid residues is effected. Zhang & Castellino, Biochemistry 29:10829 (1990).

Protein C is also post-translationally modified by β-hydroxylation of aspartic acid 71. Drakenberg et al., Proc. Nat'l Acad. Sci. USA 80: 1802 (1983). Beta-hydroxylation may be important to protein C activity. Although its function is not known it has been suggested that it may be involved in γ-carboxyglutamic acid independent $Ca^{2+}$ binding, and it may be required for full anti-coagulant activity.

Human protein C is also glycosylated. Kisiel, J. Clin. Invest. 64: 761 (1979). It contains four potential N-linked glycosylation sites, located at Asn97, Asn248, Asn313 and Asn329. The first three signals match the consensus Asn-X-Ser/Thr glycosylation sequences, and are actively glycosylated. There is an atypical glycosylation signal at Asn329, Asn-X-Cys-Ser. The Asn329 signal is glycosylated in bovine protein C, but it is not yet known if Asn329 is glycosylated in human protein C. Miletich et al., J. Biol. Chem. 265: 11397 (1990). The pattern and extent of glycosylation can alter the physiological activity of protein C.

Until recently, human protein C for experimental and therapeutic use was obtained exclusively from human plasma. Unfortunately, the quantity of protein that can be obtained from human serum is limited. Furthermore, products derived from human serum pose difficulties of reliability, purity and safety.

The expression of therapeutic proteins by recombinant DNA technology is an attractive alternative to plasma production of protein C, in that it eliminates the risk of potential contamination with blood-borne viruses and theoretically provides an unlimited supply of product. But the complexity of the post-translational modifications, as discussed above, has rendered problematic the production of commercially useable amounts of suitably active protein C by expression in a heterologous host.

In fact, it has not been possible to produce vitamin K-dependent proteins like protein C at sufficiently high levels in an active form, despite efforts to do so using a variety of expression systems. See Grinnell et al. in Volume 11 of ADVANCES IN APPLIED BIOTECHNOLOGY SERIES, Chapter 3 (Gulf Publishing Co.). In particular, any prospect for expressing protein C in mammary glands of a transgenic animal and secreting the protein into milk, see, e.g., U.S. Pat. No. 4,873,316 (1989), is clouded by the fact that protein C is normally synthesized in the liver. Even HepG2 cell lines derived from human liver produce aberrant forms of protein C. Marlar & Fair (1985).

In this regard, it has been observed that a mouse mammary epithelial cell line (C-127) transfected with a bovine papilloma virus (BPV) vector bearing the cDNA for human protein C expressed protein C that was only 30–40% active. Further analysis revealed that the protein C contained diminished levels of γ-carboxyglutamic acid and little, if any, β-hydroxyaspartic acid. Suttie et al., *Thrombosis Res.* 44: 129 (1986). These experiments indicate that mouse mammary epithelial cells cannot perform all of the post-translational modifications necessary for obtaining suitably active protein C, which in turn casts doubt on the likelihood of obtaining such protein C from the milk of a transgenic mammal.

SUMMARY OF THE INVENTION

It is therefore an object of the present invention to provide a transgenic animal which produces in its milk recombinant protein C that comprises a significantly higher percentage of active protein than has been achieved heretofore.

It is another object of the present invention to provide a process for producing protein C in commercially useable amounts, by means of a transgenic mammal.

In accomplishing the foregoing objects, there has been provided, in accordance with one aspect of the present invention, a transgenic mammal containing an exogenous DNA sequence stably integrated in its genome, wherein the exogenous DNA sequence comprises a promoter operably linked to a DNA sequence encoding a polypeptide having protein C activity and a signal peptide, wherein the promoter is specifically active in mammary cells, particularly mammary epithelial cells, and the signal peptide is effective in directing the secretion of the protein C into the milk of the transgenic mammal. In a preferred embodiment, the promoter is a whey acidic protein promoter.

In accordance with another aspect of the present invention, there has been provided a process for the production of protein C, comprising the steps of (A) providing a transgenic mammal characterized by an exogenous DNA sequence stably integrated in its genome, wherein the exogenous DNA sequence comprises a promoter operably linked to a DNA sequence encoding a polypeptide having protein C activity and a signal peptide, the promoter being specifically active in mammary cells and the signal peptide being effective in directing the secretion of the protein C into the milk of the transgenic mammal; (B) producing milk from the transgenic mammal; (C) collecting the milk; and (D) isolating the polypeptide from the milk. In one preferred embodiment, the transgenic mammal is mouse, rabbit, pig, sheep or goat.

In accordance with still another aspect of the present invention, a process has been provided for producing transgenic animals, comprising the steps of (A) providing a mixture containing a genetic construct; (B) subjecting the mixture to anion-exchange high performance liquid chromatography to obtain purified genetic construct; and thereafter (C) microinjecting an aqueous buffer solution containing the purified genetic construct into an animal embryo. In a preferred embodiment, step (B) comprises applying the mixture to an anion-exchange high performance liquid chromatography column, eluting the genetic construct from the column, and then subjecting the genetic construct to a second anion-exchange high performance liquid chromatography.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
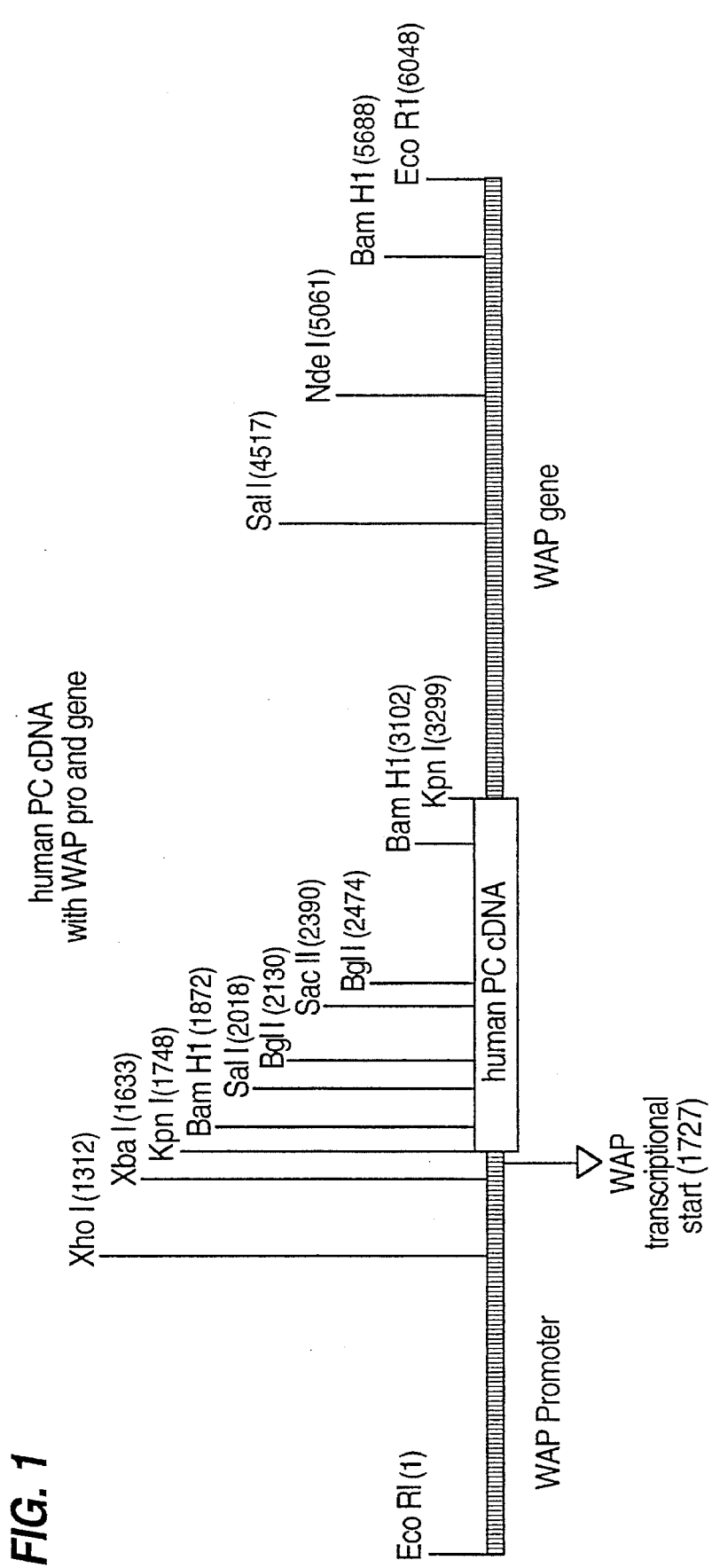
FIG. 1 is a schematic diagram representing WAPpCI, a construct which contains cDNA encoding human protein C inserted into an intact murine whey acidic protein (WAP) gene at the unique Kpn1 site.

Notwithstanding past failures to express recombinant protein C with suitably high activity in several different expression systems, including transformed mammary cells, it has been discovered that recombinant protein C characterized by a high percentage of active protein can be obtained in the milk of transgenic animals that incorporate DNAs according to the present invention. Transgenic animals of the present invention are produced by introducing into developing embryos DNA that encodes protein C, such that the DNA is stably incorporated in the DNA of germ line cells of the mature animal and inherited in normal, mendelian fashion.

In accordance with the invention, DNAs can be introduced into embryos by a variety of means to produce transgenic animals. For instance, totipotent or pluripotent stem cells can be transformed by microinjection, calcium phosphate mediated precipitation, liposome fusion, retroviral infection or by other means. The transformed cells can then be introduced into embryos and incorporated therein to form transgenic animals. In a preferred method, developing embryos can be infected with retroviral vectors and transgenic animals can be formed from the infected embryos. In the most preferred method, however, the DNAs of the invention are injected into embryos, preferably at the single-cell stage, which are allowed to develop into mature transgenic animals.

Suitable protein C-encoding DNA used for producing transgenic animals in this fashion can be obtained using human liver tissue as a source for cloning the hPC gene. The DNA coding for protein C can be fused, in proper reading frame, with appropriate regulatory signals, as described in greater detail below, to produce a genetic construct which is then amplified, for example, by propagation in a bacterial vector, according to conventional practice.

The amplified construct is thereafter excised from the vector and purified for use in microinjection. The purification is preferably accomplished by means of high performance liquid chromatography (HPLC), which rids the construct of contamination from the bacterial vector and from polysaccharides typically present when other techniques, such as conventional agarose electroelution, are used. The preferred HPLC method entails sorbing the construct onto an anion-exchange HPLC support and selectively eluting the construct from the support, preferably with an aqueous sodium chloride solution, thereby to eliminate contamination from the vector. (Elution may be effected by other means, such as a pH gradient.) Alternatively but less preferably, the excised construct can be purified by ultracentrifugation through an aqueous sucrose gradient.

Since it is preferable that the construct have the minimum amount of impurities, more than one cycle of HPLC or other purification is advantageous. In particular, the use of HPLC-purified DNA for microinjection, as described above, allows for remarkably high transformation frequencies, on the order of 20% or more in both mice and pigs.

All lactating animals, that is, all mammals, are suitable for use according to the present invention. Preferred mammals include mice, rats, rabbits, pigs, sheep, goats and cows. More particularly, mice, pigs, sheep and cows are preferred. Most preferred at present are mice, pigs and sheep.

DNA constructs useful in the present invention provide a DNA sequence encoding protein C operably linked to all the cis-acting signals necessary for mammary tissue specific expression of protein C, post-translational modification of protein C, secretion of protein C into milk, and full biological activity of protein C.

DNAs useful in the invention include genomic or complementary DNAs that encode naturally occurring protein C. In a preferred embodiment DNAs encoding human protein C are employed, including cDNA and genomic DNAs. DNAs encoding protein C from other species may also be used, such as the protein C encoded by rats, pigs, sheep, cows and chimpanzees.

Modified protein C sequences also can be employed in the present invention. Useful modifications in this context include but are not limited to those that alter the post-translational processing of protein C, that alter the size of protein C, that fuse protein C or portions thereof to portions of another protein, or that alter the active site of protein C. Preferred modifications include those that provide an activated protein C and those that provide for activation of protein C in the absence of thrombomodulin. In a preferred embodiment, modified forms of human protein C are employed.

Such modifications can be introduced into protein C by techniques well known to the art, such as the synthesis of modified genes by ligation of overlapping oligonucleotide, and by introducing mutations directly into cloned genes, as by oligonucleotide mediated mutagenesis, inter alia.

The cis-acting regulatory regions useful in the invention include the promoter used to drive expression of the protein C gene. Promoters useful in the invention are active in mammary tissue. Particularly useful are promoters that are specifically active in mammary tissue, i.e., are more active in mammary tissue than in other tissues under physiological conditions where milk is synthesized. Most preferred are promoters that are both specific to and efficient in mammary tissue. By "efficient" it is meant that the promoters are strong promoters in mammary tissue that can support the synthesis of large amounts of protein for secretion into milk.

Among such promoters, the casein, lactalbumin and lactoglobulin promoters are preferred, including, but not limited to the α-, β- and γ-casein promoters and the α-lactalbumin and β-lactoglobulin promoters. Preferred among the promoters are those from rodent (murine and rat), pigs and sheep, especially the rat β-casein promoter and the sheep β-lactoglobulin promoter. The most preferred promoters are those that regulate a whey acidic protein (WAP) gene, and the most preferred WAP promoter is the murine WAP promoter.

Also important to the invention are the signal sequences that direct secretion of protein into the milk of the transgenic animal. In this regard, both endogenous and heterologous signal sequences are useful in the invention. Generally, the signal peptides of proteins normally secreted into milk are useful in the invention. The signal sequences of proteins that occur in high concentration in milk are particularly preferred, such as the signal peptides of the caseins, lactalbumins and lactoglobulins, including, but not limited to the signal peptides of the α-, β- and γ-caseins and α-lactalbumin and β-lactoglobulin. More particularly, the signal sequence of whey acidic protein is preferred, most particularly the signal sequence of the murine whey acidic protein.

Also particularly preferred are the signal peptides of secreted coagulation factors. Especially preferred in this regard are the signal peptides of protein C, and t-PA. Most especially preferred is the secretion signal of human protein C.

Among the sequences that regulate transcription that are useful in the invention, in addition to the promoter sequences discussed above, are enhancers, splice signals, transcription termination signals and polyadenylation sites, among others. Particularly useful regulatory sequences increase the efficiency of mammary cell specific expression of protein C in transgenic animals.

Especially useful in this regard are the other transcription regulatory sequences of genes expressed at high levels in mammary cells, such as the α-, β- and γ-casein genes and the α-lactalbumin and β-lactoglobulin genes mentioned above. Preferred sources for regulatory sequences in this regard are rodents (mice and rats), pigs and sheep.

Exemplary of preferred regulatory sequences are those associated with the rat β-casein gene and the sheep β-lactoglobulin gene, respectively. The regulatory sequences most preferred for use in the present invention are those associated with whey acidic protein genes. Particularly preferred in this context are regulatory sequences of the murine whey acidic protein.

Among the sequences that regulate translation, in addition to the signal sequences discussed above, are ribosome binding sites and sequences that augment the stability the protein C mRNA. Especially useful are the translation regulatory sequences of genes expressed at high levels in mammary cells. For instance, the regulatory sequences of the α-, β- and γ-casein genes and the α-lactalbumin and β-lactoglobulin genes are preferred, especially those from rodents (mice and rats), pigs and sheep. Even more particularly preferred are the regulatory sequences of rat β-casein and the sheep β-lactoglobulin genes.

The most preferred translational regulatory sequences of the invention are those of the whey acidic protein and the protein C genes. And the most particularly preferred regulatory sequences are those of the murine whey acidic protein and human protein C, including human genomic protein C and human protein C cDNA constructs, and including human protein C cDNA constructs that contain intron sequences.

Especially useful in the present invention are sequences that advantageously modulate post-translational modifications of protein C, such that the protein C produced in the transgenic animals of the invention is active. In particular, the genomic sequences of the human protein C gene are preferred.

Thus, in accordance with the present invention a DNA sequence that encodes protein C is operably linked to cis-acting regulatory sequences which allow for efficient expression of protein C in milk. The resulting chimeric DNA is introduced into a mammalian embryo, where it integrates into the embryonic genome and becomes part of the heritable genetic endowment of all the cells, including the germ line cells, of the adult which develops from the embryo. The protein C which is expressed in the mammary tissue and secreted into the milk of a transgenic mammal obtained in this manner displays a surprisingly high percentage of active protein, as measured by enzymatic and coagulation-inhibition assays which are conventionally employed to detect protein C activity, such as ELISAs, chromogenic activity assays and coagulation inhibition assays. Levels of active protein on the order of 80% to 90% or more are characteristic of the protein C expressed in accordance with the present invention.

Obtaining milk from a transgenic animal within the present invention is accomplished by conventional means. McBurney et al., *J. Lab. Clin. Med.* 64: 485 (1964). The protein C contained in such milk can be purified by known means without unduly affecting activity. One suitable approach to purification in this regard is immunoaffinity chromatography. Alternatively, the expressed protein C can be isolated from the milk by other conventional means, for instance, by the method of Kisiel, *J. Clin. Invest.* 64: 761 (1979). In any event, it is preferred that protein C produced in milk pursuant to the present invention should be isolated as soon as possible after the milk is obtained from the transgenic mammal, thereby to mitigate any deleterious effect(s) on the stability of the protein.

The present invention is further described by reference to the following, illustrative examples.

EXAMPLE 1. DNAs useful for expressing protein C in transgenic animals

The entire murine WAP gene including 2.5 kb of 5' untranslated sequence and 3' untranslated regions was obtained from L. Hennighausen. See Campbell et al., *Nucleic Acids Res.* 12:8685 (1984). The human placental cDNA for human protein C was obtained from C. Shoemacker.

Standard recombinant DNA techniques were employed to generate the vectors and expression constructs of the preferred embodiments, and for other manipulations of DNA, as set forth below. See Sambrook et al., MOLECULAR CLONING, A LABORATORY MANUAL, Vol. 1–3 (Cold Spring Harbor Press 1989).

(1) WAPpC1

A DNA construct called WAPpC1 was made, consisting of the entire murine WAP gene containing one copy of human protein C cDNA inserted at the unique KpnI site, 24 base pairs 3' of the transcriptional start site of the WAP gene (FIG. 1). This WAP—protein C construct was ligated into a bluescribe vector (Stratagene) to facilitate further manipulation.

(2) WAPpC2

WAPpC2 is similar to WAPpC1, comprising the entire murine WAP gene and human protein C cDNA but differs from WAPpC1 in lacking artefactual 5' flanking sequences present in WAPpC1 as a result of cloning procedures used to make that construct. Specifically, 33 bp 5' to the protein C ATG and 118 "A's" at the 3' end of the protein C cDNA were removed by PCR, and new KpnI sites were added at the 5' and 3' ends.

EXAMPLE 2. Preparation of DNAs for microinjection

DNA for microinjection was prepared according to the procedures described below for DNA from WAPpC1.

The 9 kb WAPpC1 fragment was removed from the vector with the restriction enzyme EcoRI. After digestion with EcoRI the solution containing the WAPpC1 DNA was brought to 10 mM magnesium, 20 mM EDTA and 0.1% SDS and then extracted with phenol/chloroform. DNA was precipitated from the aqueous layer with 2.5 volumes of ethanol in the presence of 0.3M sodium acetate at −20° C. overnight. After centrifugation, the pellet was washed with 70% ethanol, dried, and resuspended in sterile distilled water.

DNA for microinjection was purified by HPLC. The digested DNA was precipitated with isopropanol and then dissolved in TE buffer at 0.3 µg/ml. Fragments were purified by HPLC using a Waters GEN FAX PAC HPLC column. The column was run isocratically using a buffer consisting of 25 mM Tris-HCl (pH 7.5), 1 mM sodium EDTA, and 0.63M NaCl. This is the minimum NaCl concentration that will elute the large construct fragment and results in the best resolution from the smaller vector fragment which elutes just prior to the construct fragment. About 15 µg of digested DNA was loaded on the column at a time. The construct-fragment samples from all of the chromatographic runs were then pooled, reprecipitated, and run through the column a second time. Results reported below, for both pigs and mice, were generated using HPLC-purified DNA.

DNA concentrations were determined by agarose gel electrophoresis by staining with ethidium bromide and comparing the fluorescent intensity of an aliquot of the DNA with the intensity of standards. Samples were then adjusted to 10 µg/ml and stored at −20° C., prior to microinjection.

EXAMPLE 3. Transgenic animals (1) Mice

Transgenic mice were produced essentially as described by Hogan et al., MANIPULATING THE MOUSE EMBRYO (Cold Spring Harbor Press 1986). The procedures employed are outlined below.

Glass needles for micro-injection were prepared using a micropipet puller and microforge. Injections were performed using a Nikon microscope having Hoffman Modulation Contrast optics, with Narashigi micromanipulators and a pico-injector driven by $N_2$ (Narashigi).

Fertilized mouse embryos were surgically removed from the oviducts of superovulated female CD-1 mice and placed into M2 medium. Cumulus cells were removed from the embryos with hyaluronidase at 300 µg/ml. The embryos were then rinsed in new M2 medium, and transferred into M16 medium for storage at 37° C. prior to injection.

After injecting the DNA solution into the male pronucleus, embryos were implanted into avertin-anesthetized CD-1 recipient females made pseudo-pregnant by mating with vasectomized males. Embryos were allowed to come to term and the newborn mice were analyzed for the presence of the transgene as described below.

(2) Pigs

Embryos are recovered from the oviduct. They are placed into a 1.5 ml microfuge tube containing approximately 0.5 ml embryo transfer media (phosphate buffered saline +10% fetal calf serum, Gibco BRL). These are then centrifuged for 12 minutes at 16,000×g RCF (13,450 RPM) in a microcentrifuge (Allied Instruments, model 235C). Embryos are removed from the microfuge tube with a drawn and polished Pasteur pipette and placed into a 35 mm petri dish for examination. If the cytoplasm is still opaque with lipid such that pronuclei are not visible, the embryos are centrifuged again for 15 minutes. Embryos to be microinjected are placed into a microdrop of media (approximately 100 µl) in the center of the lid of a 100 mm petri dish. Silicone oil is used to cover the microdrop and fill the lid to prevent media from evaporating. The petri dish lid containing the embryos is set onto an inverted microscope (Carl Zeiss) equipped with both a heated stage and Hoffman Modulation Contrast optics (200×final magnification). A finely drawn (Kopf Vertical Pipette Puller, model 720) and polished (Narishige microforge, model MF-35) micropipette is used to stabilize the embryos while about 1–2 picoliters of HPLC-purified DNA solution containing approximately 200–500 copies of DNA construct is delivered into the male pronucleus with another finely drawn micropipette. Embryos surviving the microinjection process as judged by morphological observation are loaded into a polypropylene tube (2 mm ID) for transfer into the recipient pig.

(3) Other animals

Methods for microinjection of other animal species are similar to the methods set forth above.

EXAMPLE 4. Assessment via PCR of WAP/hPC constructs in transgenic animals (1) Preparation of DNA form transgenic animals DNA can be prepared from tissue of a transgenic animal of any species by the method exemplified below for mice.

A 5 mm piece of mouse tail was removed from young, potentially transgenic mice at weaning (3 weeks of age), minced, and treated with proteinase K and SDS at 37° C. overnight. The mixture was then incubated with DNase-free RNase at 37° C. for 1–2 hours. DNA was precipitated from the mixture with sodium acetate and ethanol at −20° C. overnight, collected by centrifugation, washed in 70% ethanol and dried. The dried DNA pellet was used directly for PCR. In some cases the mixture was extracted extensively with phenol/chloroform prior to ethanol precipitation.

(2) Oligonucleotide probes used in the PCR assay

Figure 2:
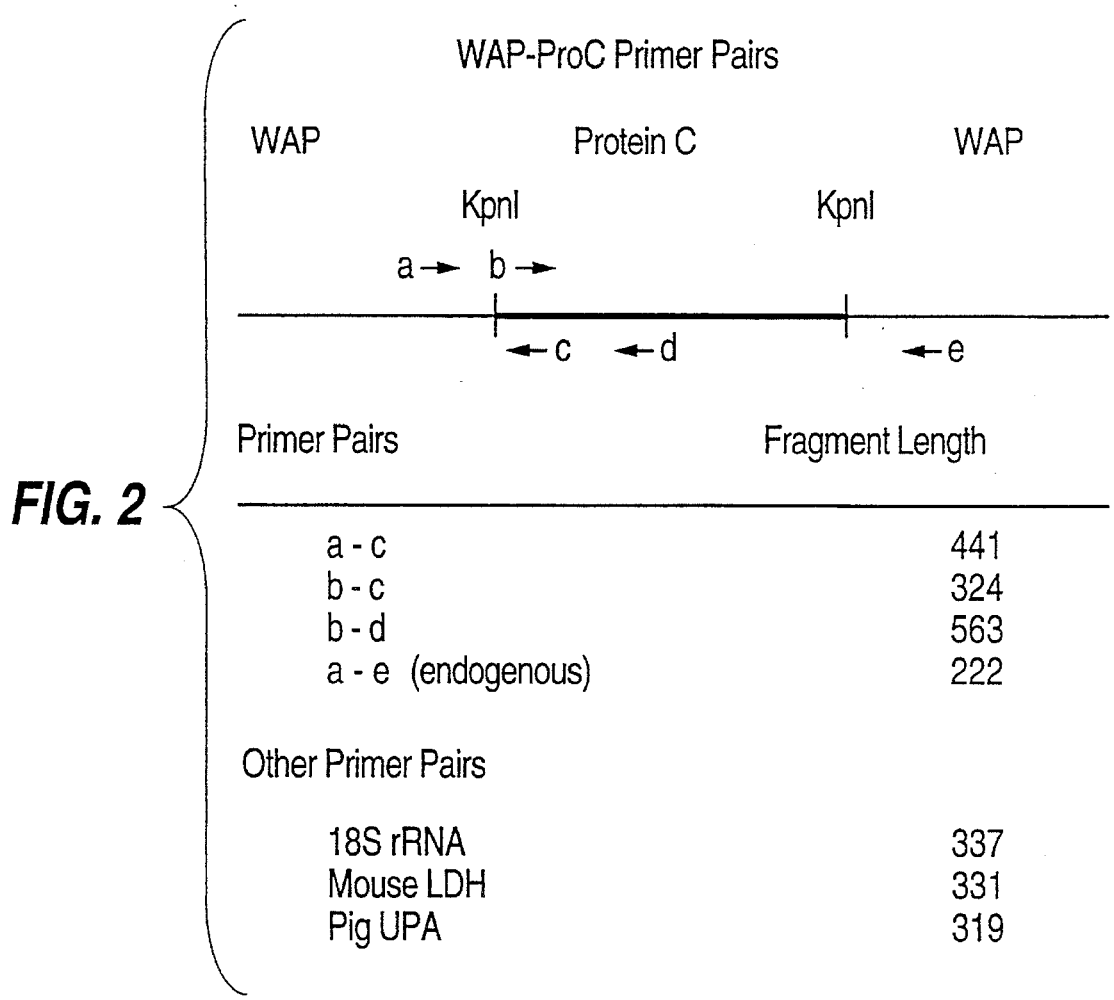
FIG. 2 is a schematic representation of polymerase chain reaction (PCR) primer pairs useful to detect WAP-protein C DNAs in transgenic animals.

Oligonucleotide pairs were used to prime polymerase chain reactions that detected the presence of WAP-protein C constructs in the transgenic animals. These pairs and their extension products are shown schematically in FIG. 2 Oligonucleotide pairs that bridge the region from the WAP sequences 5' of the KpnI site and the endogenous WAP sequences which naturally lie 3' of the KpnI site also provided positive controls in mice.

(3) PCR reaction conditions and product analysis

PCR reactions were performed using an annealing temperature of 58° C., a denaturation temperature of 94° C., and an extension temperature of 72° C., using 100 ng of oligo primers and 50 ng of (genomic) template DNA per reaction, and cycling through the temperatures 40 times using an automatic temperature cycler (M. J. Research).

PCR reactions were analyzed by running 20% of the reaction products on agarose gels and identifying fragment sizes by comparison with marker DNA fragments.

(4) Results of PCR analysis of transgenic animals

PCR analysis of potentially transgenic mice and pigs which developed from embryos microinjected with WAPpC1 and WAPpC2 constructs are summarized in Table 2. The results show that WAPpC constructs frequently integrated into the embryonic genomes of both mice and pigs. Furthermore, mendelian transmission was observed in 5 of the 16 mice which were tested.

TABLE 2

Whey Acid Protein-Protein C Construct Integration Rates

| Animal | # Tested | # Positive | Integration Rate |
|---|---|---|---|
| Mice | 105 | 30 | 29% |
| Pigs | 23 | 5 | 22% |
| Mendelian Transmission in Transgenic Mice 5/16 Tested = 31% | | | |

EXAMPLE 5. Preparation of milk and whey from transgenic animals (A) Mice: Lactating mice were milked an average of 3 times per week. The mice were first separated from their young for approximately 5 hours. They were then anesthetized with 0.4 ml avertin at 2.5% (I.M.), and 0.2 ml oxytocin was then administered at 2.5 IU/ml (I.P.) to permit release of the milk. A milking device consisting of a vacuum pump (2.5 psi) and syringe with an eppendorf tip was used to direct milk into an eppendorf tube. During collection, milk was placed on ice until all samples were obtained.

To prepare whey, milk was diluted 1:1 with TS buffer (0.03M Tris pH 7.4; 0.06 NaCl) and centrifuged in a TLA-100 rotor in a Beckman TL-100 table top ultracentrifuge at 51,000 rpm (89,000×g) for 30 minutes at 4°0 C. After centrifugation the tubes were put on ice, and the whey was collected with an 18 gauge needle, leaving the casein pellet and upper cream layer in the tube. To remove solids or cream that co-transferred during the initial recovery, the whey obtained from the first centrifugation was subjected to a second spin at 12,000 rpm for 30 minutes at 4° C. in a TMA-4 rotor in a Tomy MTX-150 centrifuge. Following the second spin the tubes were place on ice and the whey was recovered as before.

EXAMPLE 6. Determination by ELISA of protein C produced by transgenic mammals

An ELISA was used to measure the amount of protein C protein produced by transgenic animals in their milk or whey. Two monoclonal antibodies, 7D7B10 and 12A8, and a polyclonal antiserum were used in the ELISAs, and a variety of other protein C specific antibodies could be employed. The 7D7B10 monoclonal is specific for the $NH_2$ terminus of the light chain of protein C. 12A8 is specific for the reactive site on the heavy chain of protein C.

Microtiter plate wells were coated overnight at 4° C. with 3 μg/ml of monoclonal antibody in 50 μl of 0.1M sodium bicarbonate buffer, pH 8.3. The wells were washed once with TET buffer (0.01M Tris pH 7.5; 0.01M EDTA; 0.02% tween-20, pH 7.45) and then blocked with 1% BSA in PBS using 400 μl per well for 1 hour at 37° C. Plates were again washed with TET buffer (5X) followed by addition of 100 μl of sample whey or normal whey spiked with human protein C from plasma, to generate a standard curve. After washing 5X with TET buffer, horse radish peroxidase (HRP)-conjugated to rabbit anti-hPC was diluted 1:1000 in 0.1% BSA/TET and 100 μl was added per well and incubated for 2 hours at room temperature, with shaking at 100 rpm. After again washing 5 times with TET buffer, 100 μl of orthophenyldiamine (OPD), from a stock solution made by dissolving one tablet of OPD in 20 ml of 0.1M citrate-phosphate buffer (pH 5.0), were added to each well. After 10 minutes at room temperature the reaction was stopped with 1N sulfuric acid. The extent of the reaction was determined by measuring product absorption at 490 nm.

Figure 3:
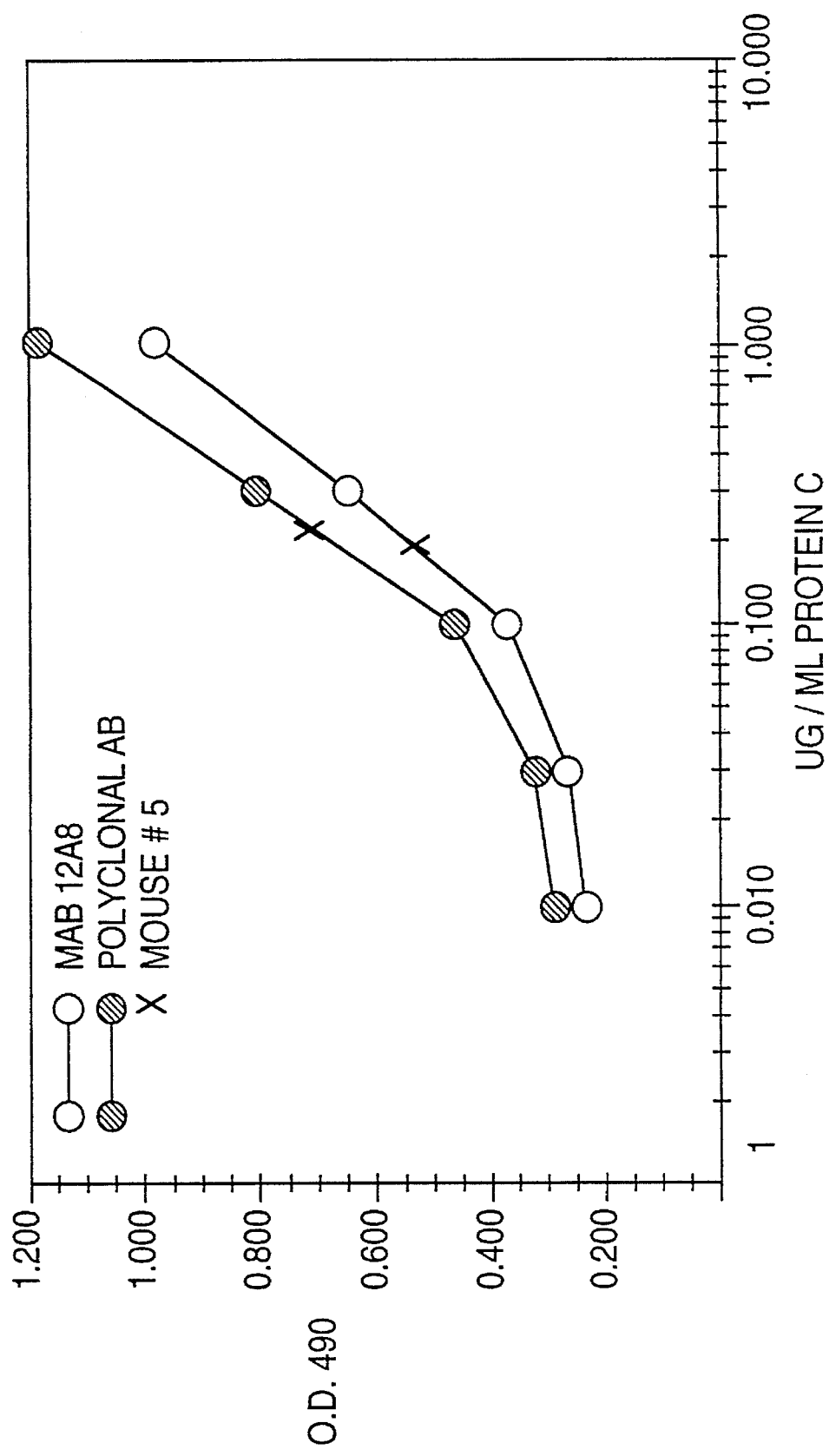
FIG. 3 is a graph that shows the results of an enzyme linked immunosorbent assay (ELISA) of human protein C in milk obtained from a transgenic mouse.

The result of an ELISA analysis of the milk from one transgenic mouse (Mouse No. 5) is shown in FIG. 3. Standard curves were obtained for a monoclonal antibody, 12AB, and a rabbit polyclonal antibody, titered against human protein C which was obtained by immunoaffinity chromatography over immobilized 7D7B10 antibody. The milk sample, taken from transgenic Mouse No. 5, contained approximately 200 ng/ml protein C.

To assure proper protein C structure as judged by immunocapture by two different monoclonal antibodies, as well as by a polyclonal mixture of antibodies, the samples for several different transgenic mice were screened by ELISAs. Table 2A shows essentially equivalent antigen levels, as judged by three different immunocaptures and detection by ELISA. The majority of mice produced by microinjection of WAPpC1 produced antigen levels in the 1-to-4-μg/ml range.

TABLE 2A hPC ANTIGEN ELISA (NG/ML)

| MOUSE ID-DAY | MONOCLONAL LC-CAPTURE | MONOCLONAL HC-CAPTURE | POLY-CLONAL CAPTURE |
|---|---|---|---|
| Y52-15 | 1320 | 3530 | 4100 |
| Y57-15 | 930 | 1150 | 2880 |

The concentration of human protein C in whey obtained from transgenic mice, as well as milk, was also determined in this manner, with equivalent results.

Similar assays were routinely carried out to assay protein C in milk obtained from transgenic animals. Results obtained using the 7D7B10 antibody in light-chain capture ELISAs are compiled in Table 3, which summarizes the concentration of protein C in milk obtained from transgenic mice during the first four lactation periods. Dashes indicate that no test was done. All of the animals provided significant levels of protein C in their milk. Preliminary results also indicate that the second lactation period is sometimes superior to the other periods tested.

TABLE 3 hPC ELISA SCREENING (LIGHT CHAIN CAPTURE)

| | PC-Ag (μg/ml) Day of Lactation | | | |
|---|---|---|---|---|
| MOUSE ID | 5–6 | 8–9 | 11–12 | 13–15 |
| Y68-L2 | — | 1.05 | — | — |
| Y51-L2 | — | 1.08 | — | 0.56 |
| Y51-L3 | — | 2.80 | 1.30 | 1.79 |
| Y52-L1 | — | 0.55 | 0.65 | — |
| Y52-L2 | — | 1.52 | — | 0.95 |
| Y57-L1 | — | — | 0.52 | 1.35 |
| Y57-L2 | 1.47 | — | 0.98 | — |
| R03-L2 | 1.90 | 2.88 | 3.01 | — |
| R12-L1 | — | 0.60 | — | — |
| R12-L2 | — | 2.98 | 2.48 | 2.40 |

Human protein C in the milk obtained from other species can be measured by the same methods. Thus, protein C from human plasma spiked into pig milk was accurately detected via the above-described ELISA.

EXAMPLE 7. Assay for protein C amidolytic activity using the chromogenic substrate S-2366

The enzymatic activity of protein C in the milk of transgenic animals was measured directly using a chromogenic assay essentially as described by Odegaard et al., *Haemostasis* 17:109 (1989). In this assay microtiter plate wells were coated with the 7D7B10 monoclonal antibody (50 μg/ml) in 50 μl of 0.1M bicarbonate buffer, pH 8.6 at 4° C. overnight. Plates were then rinsed with TET buffer (0.1M Tris; 0.03M EDTA; 0.05% tween-20) and blocked with 400 μl/well 1% BSA in PBS and incubated at room temperature for 1 to 1.5 hours. After rinsing 3 times with TET buffer, 50 μl of whey sample and 50 μl of 0.1M Tris pH 7.5, 0.03M EDTA was added per well and incubated at room temperature for 2 hours. Plates were washed 3 times in TET buffer. The captured human protein C was activated by adding 120 μl of Protac™, a commercial reagent containing a snake-venom enzyme (12 ml distilled water per vial), 30 μl TSP buffer and 0.1% BSA, pH 7.5, per well. After incubation for 6–10 minutes at room temperature, 120 μl S-2366 (Kabi substrate) at 25 mg/10.8 ml Tris pH 7.8 was added to each well and the plates were incubated for 2–8 hours at room temperature, or several days at 4° C. The amount of protein C activity in each sample was determined by measuring formation of the reaction product by absorption at 405 mm.

Results obtained using milk and whey from a transgenic mouse and the pooled milk and whey of several transgenic mice appear in Table 4, which shows the amount and the specific activity of protein C in the samples. Note that the samples were obtained either during the first lactation period, L1, or were obtained from a second and third lactation, L2 and L3. The specific activity of the human protein C obtained from transgenic mice determined in these assays, 205 units (U) per mg, is similar to that of human protein C of similar purity obtained from natural sources. (A "unit" is defined by pooling blood from many individuals and determining activity in 1 ml of the pooled blood.)

TABLE 4

| | Protac ™-Specific Amidolytic Activity Upon S-2366 | | |
|---|---|---|---|
| | U/ml | μg Ag/ml | U/mg |
| Reconstituted Whey Y52-L1 Pool* | 0.07 | 0.34 | 206 |
| Y52-L1 Milk Pool* | 0.23 | 1.12 | |
| Transgenic Whey Pool** | 1.12 | 0.55 | 205 |
| Transgenic Milk Pool** | 0.43 | 2.10 | |

*Pooled milk from days 5–15.
**L2 and L3 from mice Y51, Y52, Y57, R03, R12.

EXAMPLE 8. Determination of protein C produced in transgenic mammals by activated partial thromboplastin clotting time assay The activity of protein C was also measured in a clotting time assay, the activated partial thromboplastin clotting time assay (APTT). In this assay, each well of a plastic Coag-a-mate tray received 90 μl of PC-deficient plasma plus 10 μl of an APC standard or unknown, diluted with Tris/saline/BSA. The tray was then placed on an automated analyzer (APTT mode, 240 second activation). The run was started, which automatically performed the addition of 100 μl of APTT reagent and 100 μl of 0.025M $CaCl_2$. Data obtained using a standard APC preparation was fitted to the equation $y=ax+b$ where y=clotting time and x=APC, which was then used to determine the amount of APC in a sample.

Figure 4:
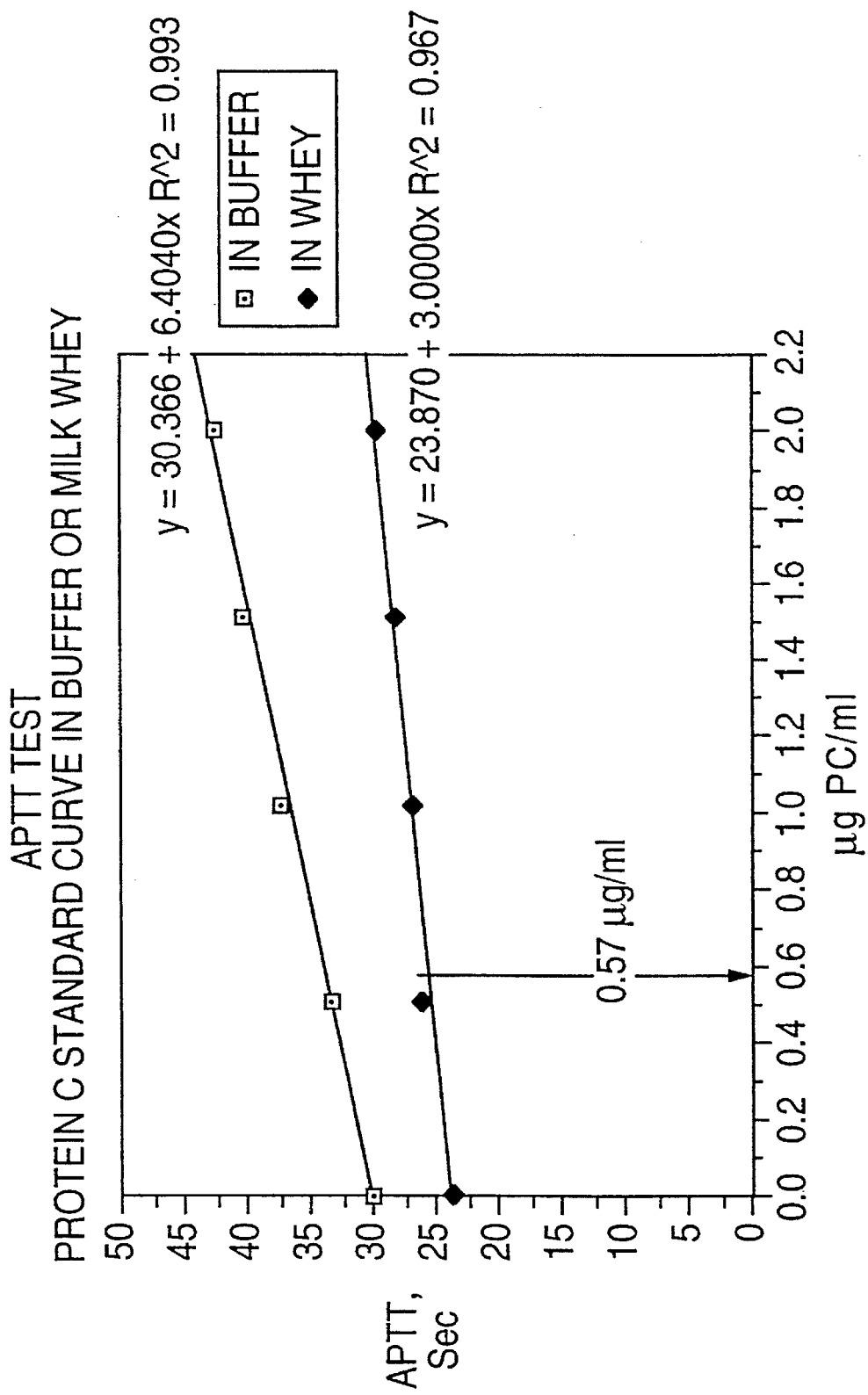
FIG. 4 is a graph that shows the results of an APTT assay to determine human protein C anticoagulant activity in whey obtained from a transgenic mouse.
Figure 5:
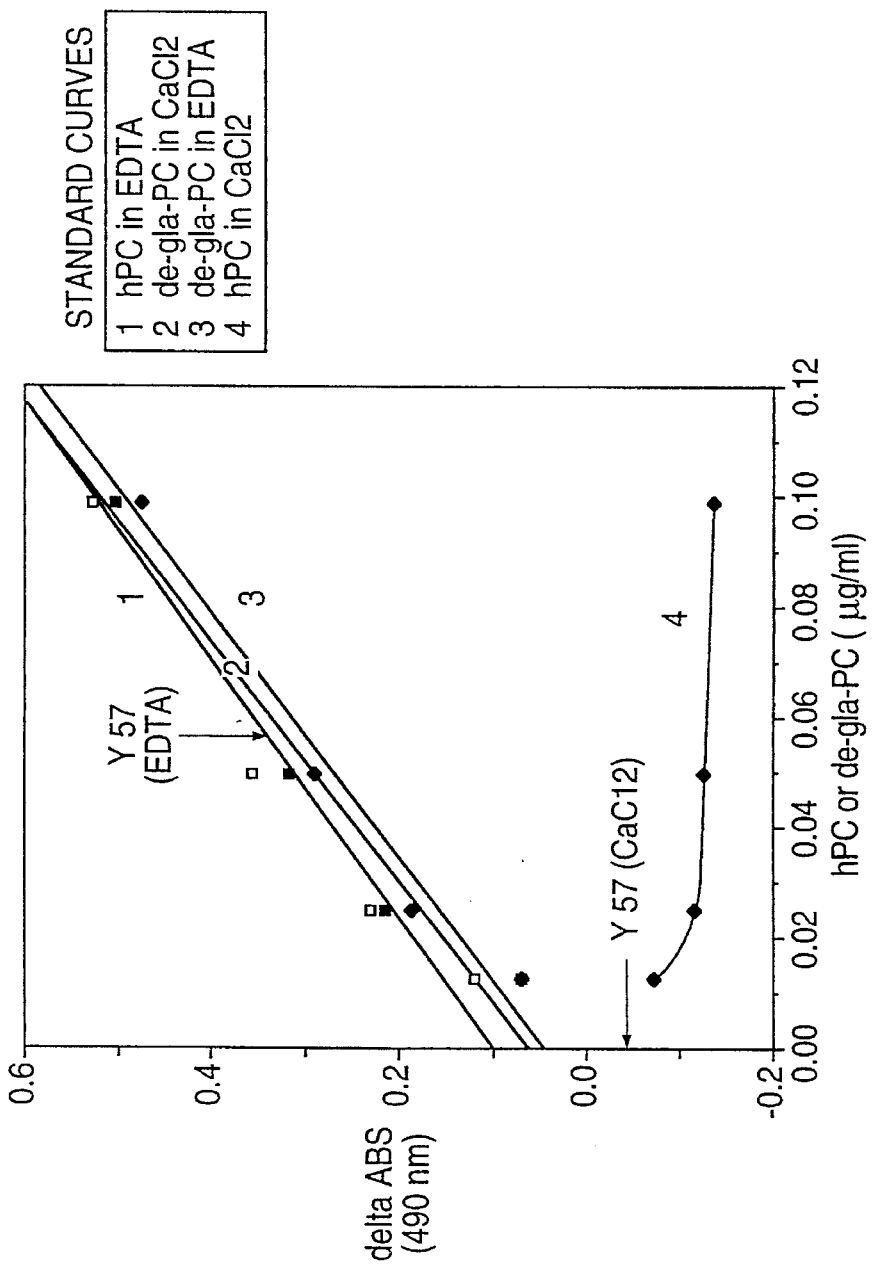
FIG. 5 is a graph that shows the results of $Ca^{2+}$-dependent and $Ca^{2+}$-independent light chain capture ELISAs which demonstrate that the γ-carboxyglutamic acid in human protein C in whey from transgenic mouse Y52 is similar to that in protein C derived from human serum.

The result of an APTT assay of whey pooled from transgenic mice is shown in FIG. 4. The standard curves in the figure correlate the activity determined by the APTT assay with the amount of active human protein C in mouse milk or mouse whey. The activity in the APTT assay of the whey sample obtained from the transgenic mouse corresponded to a concentration of approximately 0.57 μg/ml, interpolated from the standard curve for human protein C in whey. An ELISA (not shown) of the same whey sample detected approximately 0.60 μg/ml of human protein C, as protein. Thus, within the normal range of error of these assays, human protein C produced in transgenic mice is as active as the control human protein C.

EXAMPLE 9. Mapping of Calcium Dependent Conformer by Metal-Dependent Immunoaffinity Standard ELISAs were run in normal mouse milk whey with varying concentrations of hPC or hPC without Gla regions in the presence of 25 mM EDTA. After capture by 7D7B10, an assay replicating that effected with 25 mM EDTA was treated with several washes of 25 mM $CaCl_2$, and then was followed by the ELISA detection protocol described previously. While de-Gla protein remained bound to the capture antibody in the presence of $CaCl_2$, the PC standard did not remain bound in the presence of added $CaCl_2$. It was observed that whey from the transgenic mouse Y57 behaved in a similar manner to the γ-carboxylated native PC, suggesting that it is also γ-carboxylated like the native molecule.

EXAMPLE 10. Purification of human protein C from the milk of transgenic animals (1) Preparation of whey samples Milk from several WAPpC1 transgenic mouse lines was pooled, chilled on ice, diluted 6-fold with 50 mM Tris-HCl, 0.15M NaCl pH 7.2 (TBS) (1 ml milk per 5 ml TBS), and centrifuged at 125,000×g for 30 minutes at 4° C. Following centrifugation, the whey was collected and pooled using a pasteur pipet and pooled, being careful not to disturb the fatty overlayer or the casein pellet. Samples were removed from the pool for later assay and then both the samples and the pooled whey were frozen and stored at −90° C. Human protein C in samples was determined by ELISA, as described above.

Individual whey pools were thawed at 2° CC, combined, and the amount of human protein C (hPC) in the combined pool was determined by ELISA using the 7D7B10 monoclonal antibody (Mab). The combined pool contained approximately 30 μg hPC, determined by this assay, which was within 20% of the total determined by adding determinations of the individual pools.

The combined pool, approximately 150 ml, was dialyzed (14,000 MW cutoff) against 25 mM EDTA-TBS diluted 5-fold with pure water. The dialyzed whey was concentrated 5-fold by lyophilization and subsequent reconstitution with nanopure water, to yield a final buffer concentration equivalent to 25 mM EDTA in TBS, and a 5-fold increase in protein concentration. The concentrated whey contained 930 mg protein, as estimated by optical absorption at 280 nm, at 16 mg/ml.

(2) Immunoaffinity chromatography

The resin immunosorbent (Affiprep™) used to purify human protein C in the whey of transgenic mice contained 3.3 mg 7D7B10 Mab/ml of Affiprep resin. The 7d7B10 Affiprep resin was assessed by mock immunopurification using 30 μg of plasma derived hPC doped into control (nontransgenic) mouse whey. Approximately the same relative amount of total protein was loaded onto the column (660 mg on a 10 mL Affiprep) and otherwise processed as described below.

Freshly concentrated whey (16 mg/ml, 930 mg total protein, as determined by optical absorption at 280 nm) was batch-loaded onto 13 ml of 7D7B10 Affiprep containing 3.3 mg 7D7B10 Mab/ml resin for 4 hours at 2° C., without addition of carrier protein. The column was fresh and the high total (background) protein loading was thought to be enough to condition the column. The resin was then loaded into a 1 cm diameter column and washed with 25 mM EDTA-TBS until baseline optical density (O.D.) was detected at 280 nm (3 column volumes to obtain <0.0005 O.D.)

The column was then eluted with 25 mM $CaCl_2$ in TBS pH 7.2, followed by 100 mM $CaCl_2$ in TBS, followed by 4M NaCl, followed by 2M Na thiocyanate at 0.5 ml/min. The column was re-equilibrated with 5 column volumes of 25 mM EDTA-TBS, 0.02% sodium azide.

All peak pools were dialyzed in a 100-fold dilution (by nanopure water) of 50 mM imidazole, 0.1M NaCl buffer using a 14,000 MW cutoff dialysis tubing, then lyophilized, then reconstituted to 50 mM imidazole, 0.1 NaCl buffer strength using nanopure water resulting in a 100-fold concentration of protein.

Samples of these eluate pool concentrates were prepared as per the method of Laemmli (1970), applied to a 15 well, 9 cm×2 cm, 4% stacking gel above a 7.5 cm, 7.5% resolving (30%: 2.7% bis) sodium dodecylsulphate polyacrylamide gel and electrophoresed (SDS-PAGE). After electrophoresis, the gel was stained with 1.25% Coomassie Blue dye solution.

The area of the eluate peaks obtained from immunopurification of whey from WAPpC1-transgenic mice was found to be very similar to the mock trial using an equivalent amount of (plasma derived) hPC-doped whey from control mice. Assay of 100-fold concentrated 25 mM $CaCl_2$ eluate product from WAPpC1 transgenics showed 40% yield based upon densitometry of SDS-PAGE stained with Coomassie Blue (yield not determined for mock purification). The total peak areas from mock- and WAPpC1-whey were approximately the same for all eluate peaks including the 2M Na thiocyanate peak. Approximately 2 µg of hPC antigen (ELISA with immunocapture using 7D7B10 Mab) was detected in the column fallthrough which had been combined with EDTA-TBS wash. Approximately 14 µg of hPC was detected in the 25 mM $Ca^{2+}$ eluate pool, less than 0.1 µg hPC antigen in the 100 mM $Ca^{2+}$ eluate pool, no hPC antigen was detected in the 4M NaCl pool, approximately 10 µg of hPC was detected in the 2M Na thiocynate eluate pool. Thus, 87% of the hPC antigen applied to the column was accounted for in the total antigen recovered from column effluents. A 47% antigen yield was obtained based upon the hPC antigen recovered in the 25 mM $Ca^{2+}$ eluate peak.

The starting whey applied to the column, the 2M sodium thiocyanate eluate, the 25 mM $Ca^{2+}$ eluate product, and a reference hPC derived from plasma by the American Red Cross (Lot #28300277, supplied by Dr. Carolyn Orthner) were analyzed by SDS-PAGE, both reduced and non-reduced. The 2M sodium thiocynate and 25 mM $Ca^{2+}$ eluate pools were concentrated as described above and 4 µg of antigen applied to the gel for each lane. The immunopurified hPC reference was applied to the gel as 4 µg total protein based upon O.D. at 280 nm. Scanning densitometry of this reference hPC indicated that the sample was greater than 99% pure on nonreduced SDS-PAGE, and 71% pure on reduced SDS-PAGE. Subsequent antigen assays performed on the hPC reference material indicated the concentration of the sample to be such that only 2.7 µg of the reference sample was applied to the gel. The 25 mM $Ca^{2+}$ eluate product is greater than 94% pure based upon non-reduced SDS-PAGE and 86% pure based upon reduced SDS-PAGE. The staining intensity of the 25 mM $Ca^{2+}$ eluate lanes is consistent with our previous experience for 4 µg antigen applications. The bands corresponding to reference hPC possessed lighter intensity relative to the 25 mM $Ca^{2+}$ eluate. A slightly split band at approximately 62,000 relative molecular weight (Mr) is seen for both the non-reduced reference hPC and the 25 mM $Ca^{2+}$ eluate. A doublet at about 40,000 Mr and a diffuse single band at 22,000 Mr is seen for both the reduced reference hPC and 25 mM $Ca^{2+}$ eluate. The 22,000 Mr band appearing in the hPC reference is seen to be somewhat more diffuse or heterogeneous than the similar band appearing in the 25 mM $Ca^{2+}$ eluate from the whey of transgenic mice. The sodium thiocyanate peak showed a band in excess of 180,000 Mr in the nonreduced sample and multiple bands at 50,000 Mr and 25,000 Mr in the reduced sample.

The chromatography of the WAPpC1-whey was nearly identical to the mock run using plasma-derived hPC doped into control whey. The total areas and yields of hPC in the 25 mM $Ca^{2+}$ eluates and areas of 2M sodium thiocyanate peaks for both runs were similar and thus the binding characteristics of the 7D7B10 Mab onto transgenic hPC or plasma-derived hPC were similar. This is consistent with the similarity found between plasma-derived and transgenic hPC $Ca^{2+}$- dependent conformers as judged by ELISA assays using the 7D7B10 Mab to immunocapture from whey. The primary structure as judged by SDS-PAGE appears to be similar, with the amount of α-form and β-form heavy chain being essentially the same for plasma-derived and transgenic hPC; the transgenic having 68% α-form and 32% β-form while the plasma-derived material possessed 69% α-form and 31% β-form. The light chains were also similar in size for both reference and transgenic hPC.

Previous experience with SDS-PAGE using Coomassie Blue staining of hPC has shown linearity for both chains over the range of 2–5 µg hPC applied to the gel. Thus, much of the elements of post-translational, proteolytic processing appears to have occurred properly in the mammary tissue.

The purity of these runs also demonstrates the satisfactory utility of the immunopurification procedure developed for the murine system. It is believed that the tight binding of the hPC antigen found by ELISA in the 2M thiocyanate peak of the whey from transgenic mice (assay not done for mock run) is typical of yields found for fresh immunosorbents and not due to an aberrant hPC structure. The total background protein did not seem to condition the column and thus the interaction is thought to be specific with the 7D7B10 Mab. Overall, this two step procedure results in a minimum purification factor of 27,000 for the hPC recovered from mouse milk. A large-scale purification process could employ a citrate or EDTA precipitation coupled with low speed centrifugation in place of the ultracentrifugation step used for mouse milk.

Both amidolytic and anti-coagulant assays were performed upon immunopurified milk from transgenic mice. Within the sensitivity of these assays, the amidolytic and anti-coagulant activity was the same as plasma-derived immunopurified protein C. For both types of assays, the specific activity was greater than 270 U/mg.

What we claim is:

1. A transgenic non-human mammal that contains and expresses a human protein C DNA construct in the cells of its mammary gland, wherein the DNA construct consists of:

(a) a mammary gland promoter, (b) a nucleotide sequence that encodes a signal peptide, wherein said signal peptide is effective in directing the secretion of an associated polypeptide into the milk of said transgenic non-human mammal, and wherein said signal peptide-encoding nucleotide sequence is operatively associated with said mammary gland promoter, and (c) a nucleotide sequence encoding human protein C that is operatively associated with said signal peptide-encoding nucleotide sequence, wherein human protein C is secreted into the milk of said transgenic non-human mammal, and when purified, said protein C has a specific activity more than about 80% of the specific activity of human protein C isolated from human plasma, as determined by an assay of protein C serine protease activity or anticoagulant activity, and wherein said non-human mammal is selected from the group consisting of mouse, pig, sheep, goat and cattle.

2. The transgenic non-human mammal of claim 1, wherein said promoter is selected from the group consisting of a whey acidic protein promoter, a casein promoter, a lactalbumin promoter and a β-lactoglobulin promoter.

3. The transgenic non-human mammal of claim 2, wherein promoter is a whey acidic protein promoter or a β-lactoglobulin promoter.

4. The transgenic non-human mammal of claim 3, wherein said promoter is a whey acidic protein promoter.

5. The transgenic non-human mammal of claim 1, wherein said human protein C isolated from said transgenic non-human mammal has a specific activity that is about 80% to about 100% of the specific activity of human protein C isolated from human plasma.

6. The transgenic non-human mammal of claim 5, wherein said specific activity is determined by an activated partial thromboplastin clotting time assay.

7. The transgenic non-human mammal of claim 5, wherein said promoter is a whey acidic protein promoter or a β-lactoglobulin promoter.

8. A process for the production of protein C, comprising the steps of:
 (a) providing a transgenic non-human mammal that contains and expresses a human protein C DNA construct in the cells of its mammary gland, wherein the DNA construct consists of:
  (i) a mammary gland promoter,
  (ii) a nucleotide sequence that encodes a signal peptide, wherein said signal peptide is effective in directing the secretion of an associated polypeptide into the milk of said transgenic non-human mammal, and wherein said signal peptide-encoding nucleotide sequence is operatively associated with said mammary gland promoter, and
  (iii) a nucleotide sequence encoding human protein C that is operatively associated with said signal peptide-encoding nucleotide sequence,
 wherein human protein C is secreted into the milk of said transgenic non-human mammal, and when purified, said protein C has a specific activity more than about 80% of the specific activity of human protein C isolated from human plasma, as determined by an assay of protein C serine protease activity or anticoagulant activity, and
 wherein said non-human mammal is selected from the group consisting of mouse, pig, sheep, goat and cattle,
 (b) producing milk from said transgenic non-human mammal,
 (c) collecting said milk, and
 (d) isolating said protein C from said milk.

9. The process of claim 8, wherein said promoter is selected from the group consisting of a whey acidic protein promoter, a casein promoter, a lactalbumin promoter and a β-lactoglobulin promoter.

10. The process of claim 9, wherein promoter is a whey acidic protein promoter or a β-lactoglobulin promoter.

11. The process of claim 10, wherein said promoter is a whey acidic protein promoter.

12. The transgenic non-human mammal of claim 8, wherein said human protein C isolated from said transgenic non-human mammal has a specific activity that is about 80% to about 100% of the specific activity of human protein C isolated from human plasma.

13. The transgenic non-human mammal of claim 12, wherein said specific activity is determined by an activated partial thromboplastin clotting time assay.

14. The transgenic non-human mammal of claim 13, wherein said promoter is a whey acidic protein promoter or a β-lactoglobulin promoter.

15. A transgenic non-human mammal that contains and expresses a human protein C DNA construct in the cells of its mammary gland, wherein the DNA construct consists of:
 (a) a mammary gland promoter selected from the group consisting of a whey acidic protein promoter, a casein promoter, a lactalbumin promoter and a β-lactoglobulin promoter,
 (b) a nucleotide sequence that encodes a signal peptide, wherein said signal peptide is effective in directing the secretion of an associated polypeptide into the milk of said transgenic non-human mammal, and wherein said signal peptide-encoding nucleotide sequence is operatively associated with said mammary gland promoter, and
 (c) a nucleotide sequence encoding human protein C that is operatively associated with said signal peptide-encoding nucleotide sequence,
 wherein human protein C is secreted into the milk of said transgenic non-human mammal, and when purified, said protein C has a specific activity more than about 80% of the specific activity of human protein C isolated from human plasma, as determined by an assay of protein C serine protease activity or anticoagulant activity, and
 wherein said non-human mammal is selected from the group consisting of mouse, pig, sheep, goat and cattle.

16. The transgenic non-human mammal of claim 15, wherein said human protein C isolated from said transgenic non-human mammal has a specific activity that is about 80% to about 100% of the specific activity of human protein C isolated from human plasma.

17. The transgenic non-human mammal of claim 16, wherein said specific activity is determined by an activated partial thromboplastin clotting time assay.

18. A process for the production of protein C, comprising the steps of:
 (a) providing a transgenic non-human mammal that contains and expresses a human protein C DNA construct in the cells of its mammary gland, wherein the DNA construct consists of:
  (i) a mammary gland promoter selected from the group consisting of a whey acidic protein promoter, a casein promoter, a lactalbumin promoter and a β-lactoglobulin promoter,
  (ii) a nucleotide sequence that encodes a signal peptide, wherein said signal peptide is effective in directing the secretion of an associated polypeptide into the milk of said transgenic non-human mammal, and wherein said signal peptide-encoding nucleotide sequence is operatively associated with said mammary gland promoter, and
  (iii) a nucleotide sequence encoding human protein C that is operatively associated with said signal peptide-encoding nucleotide sequence,
 wherein human protein C is secreted into the milk of said transgenic non-human mammal, and when purified, said protein C has a specific activity more than about 80% of the specific activity of human protein C isolated from human plasma, as determined by an assay of protein C serine protease activity or anticoagulant activity, and
 wherein said non-human mammal is selected from the group consisting of mouse, pig, sheep, goat and cattle,
 (b) producing milk from said transgenic non-human mammal,
 (c) collecting said milk, and
 (d) isolating said protein C from said milk.

19. The transgenic non-human mammal of claim 18, wherein said human protein C isolated from said transgenic non-human mammal has a specific activity that is about 80% to about 100% of the specific activity of human protein C isolated from human plasma.

20. The transgenic non-human mammal of claim 19, wherein said specific activity is determined by an activated partial thromboplastin clotting time assay.

* * * * *